(12) United States Patent
Ozee et al.

(10) Patent No.: US 9,675,532 B2
(45) Date of Patent: Jun. 13, 2017

(54) FLUID COSMETIC COMPOSITION COMPRISING A MONOALCOHOL

(75) Inventors: Emmanuelle Ozee, Thiais (FR); Anne-Marie Lezoray, Villeconin (FR)

(73) Assignee: L'OREAL, Paris (FR)

( * ) Notice: Subject to any disclaimer, the term of this patent is extended or adjusted under 35 U.S.C. 154(b) by 497 days.

(21) Appl. No.: 12/681,834

(22) PCT Filed: Oct. 8, 2008

(86) PCT No.: PCT/IB2008/054126
§ 371 (c)(1),
(2), (4) Date: Jun. 18, 2010

(87) PCT Pub. No.: WO2009/047718
PCT Pub. Date: Apr. 16, 2009

(65) Prior Publication Data
US 2010/0285076 A1 Nov. 11, 2010

Related U.S. Application Data

(60) Provisional application No. 60/996,701, filed on Nov. 30, 2007.

(30) Foreign Application Priority Data

Oct. 8, 2007 (FR) ...................... 07 58150

(51) Int. Cl.
| | |
|---|---|
| *A61K 8/06* | (2006.01) |
| *A61K 8/34* | (2006.01) |
| *A61K 8/89* | (2006.01) |
| *A61Q 1/02* | (2006.01) |
| *A61K 8/894* | (2006.01) |

(52) U.S. Cl.
CPC ............... *A61K 8/064* (2013.01); *A61K 8/34* (2013.01); *A61K 8/342* (2013.01); *A61K 8/894* (2013.01); *A61Q 1/02* (2013.01)

(58) Field of Classification Search
CPC ...................................... A61K 8/064
See application file for complete search history.

(56) References Cited

U.S. PATENT DOCUMENTS

| | | | |
|---|---|---|---|
| 5,393,518 A * | 2/1995 | Kwass ............................ | 424/66 |
| 5,800,816 A * | 9/1998 | Brieva et al. ................... | 424/63 |
| 5,925,338 A * | 7/1999 | Karassik et al. ................ | 424/65 |
| 5,942,213 A | 8/1999 | Bara et al. | |
| 6,426,079 B1 * | 7/2002 | Bara et al. ..................... | 424/401 |
| 7,378,103 B2 * | 5/2008 | Kanji et al. .................... | 424/401 |
| 2002/0037302 A1 | 3/2002 | Afriat | |
| 2005/0002890 A1 * | 1/2005 | Gardel et al. ............... | 424/70.16 |
| 2005/0002976 A1 * | 1/2005 | Wu ............................... | 424/401 |
| 2005/0074420 A1 * | 4/2005 | Bourdel et al. ............. | 424/70.12 |
| 2005/0220728 A1 * | 10/2005 | Kanji et al. ..................... | 424/59 |
| 2006/0013793 A1 * | 1/2006 | Themens .................... | 424/70.12 |
| 2006/0034875 A1 | 2/2006 | Nakanishi et al. | |

FOREIGN PATENT DOCUMENTS

| | | |
|---|---|---|
| EP | 1 088 540 | 4/2001 |
| FR | 2 686 510 | 7/1993 |
| FR | 1 064 909 | 1/2001 |
| FR | 2 810 541 | 12/2001 |
| FR | 2 859 627 | 3/2005 |
| JP | H06-100413 | 4/1994 |
| JP | H09-59126 | 3/1997 |
| JP | 2000/256172 | 9/2000 |
| JP | 2004/018415 | 1/2004 |
| WO | 2004 112744 | 12/2004 |

OTHER PUBLICATIONS

Notice of Reasons for Rejection issued in Japanese App. No. 2010-527593, Aug. 27, 2013.
English Translation of Relevant Parts of the Technical Examination Report Related to the Brazilian Patent Application PI 0819078-0.
Notice of Reexamination, State Intellectual Property Office of the People's Republic of China (Application No. 200880110690.9). Date of Notification: May 28, 2014.

* cited by examiner

*Primary Examiner* — Mark V Stevens
(74) *Attorney, Agent, or Firm* — Oblon, McClelland, Maier & Neustadt, L.L.P.

(57) ABSTRACT

The present invention relates to the field of making up and/or caring for the skin and is targeted in particular at providing a fluid care and/or make-up cosmetic composition in the form of a water-in-oil emulsion dedicated to the skin comprising a fatty phase, an aqueous phase and at least one dimethicone copolyol, the aqueous phase forming 40 to 60% by weight, with respect to the total weight of the composition, and comprising at least 5% by weight, with respect to the total weight of the composition, of at least one $C_2$ to $C_8$ monoalcohol.

21 Claims, No Drawings

FLUID COSMETIC COMPOSITION COMPRISING A MONOALCOHOL

The present invention relates to the field of making up and/or caring for the skin and is targeted in particular at providing cosmetic compositions, in particular fluid cosmetic compositions, which are nevertheless stable on storage and in addition capable, on application, of providing a "fresh" effect. Another subject-matter of the invention is a corresponding make-up method.

The composition can in particular be a foundation to be applied to the face or neck, a concealer, a tinted cream and a composition for making up the body.

Foundation compositions are commonly used to contribute an attractive colour to the skin, in particular to the face, but also to conceal imperfections of the skin, such as red blotches or blemishes. Many corresponding formulations have to date been developed which can in particular be differentiated from one another according to whether they have a fluid structure or a solid structure.

The present invention is more particularly concerned with compositions having a texture which is sufficiently fluid to be compatible with application with the fingers by the user. They are generally water-in-oil emulsions which may unfortunately sometimes have to be rehomogenised by agitation before use in order in particular to redisperse the pulverulent phase therein, the pulverulent phase which they comprise generally being present in a large amount. In fact, these compositions can comprise at least 10% by weight, indeed even more than 20% by weight, of filler(s) and/or pigment(s).

Thus, the document FR-A-2686510 already describes water-in-oil foundation emulsions comprising, as surfactant, an alkyl dimethicone copolyol, in particular a cetyl dimethicone copolyol. However, when these fluid emulsions comprise a large amount of volatile oils, such as, for example, cyclopentasiloxane, they are not stable over time: the emulsion, after storage for 4 months, indeed even 2 months, at ambient temperature (25° C.), releases oil at the surface of the composition and is thus no longer homogeneous. What is more, if this type of composition is not agitated, indeed even poorly agitated, the application of this composition to the skin leaves a feeling of greasiness. In point of fact, for obvious reasons, this feeling is particularly uncomfortable for the user.

One alternative in compensating for the latter disadvantage is to formulate, in the aqueous phase of these emulsions, an effective amount of alcohol which has in particular the effect of providing, on application, a feeling of freshness which is in contrast particularly appreciated by the user. Furthermore, an alcohol is naturally endowed with an antimicrobial activity when a sufficient amount of it is employed. Consequently, it makes it possible to dispense with or, failing that, to significantly reduce the amounts of chemical preservatives, such as parabens, the presence of which is required in cosmetic compositions in order to guarantee that they will remain harmless for a prolonged period of time.

Unfortunately, these emulsions, which comprise an excessively large amount of alcohol in their aqueous phase, also present a concern in terms of stability. The corresponding compositions are naturally subject to a phenomenon of phase separation. What is more, it becomes difficult to stabilise large amounts of fillers therein. These fillers have a tendency to settle out.

The aim of the present invention is specifically to provide compositions of water-in-oil emulsion type which in particular satisfy all the abovementioned requirements.

Thus, according to a first aspect, a subject-matter of the present invention is a fluid care and/or make-up cosmetic composition in the form of a water-in-oil emulsion dedicated to the skin comprising a fatty phase, an aqueous phase and at least one dimethicone copolyol, the aqueous phase forming from 40% to 60% by weight of the said composition and comprising at least 5% by weight, with respect to the total weight of the composition, of at least one monoalcohol of 2 to 8 carbon atoms.

Another subject-matter of the invention is a cosmetic method for making up the skin, comprising the application, to the said skin, of a composition as defined above.

A further subject-matter of the invention is the use of a lower monoalcohol of 2 to 8 carbon atoms in combination with a dimethicone copolyol in the preparation of a fluid make-up composition in the form of a water-in-oil emulsion, which composition is stabilised and capable of providing a feeling of freshness on application to the skin.

The invention is additionally targeted at the use of at least one dimethicone copolyol for stabilising a cosmetic composition of oil-in-water emulsion type comprising at least 40% by weight of an aqueous phase and comprising at least 5% by weight of at least one lower monoalcohol of 2 to 8 carbon atoms, with respect to the total weight of the composition.

Thus, unexpectedly, the inventors have found that the compositions according to the invention prove to exhibit a very good stability at ambient temperature (25° C.), in particular after storing for 2 months or better still for 4 months. They are easily applied to the skin, are distributed homogeneously over the skin, dry rapidly after application and provide the user, on application, with a feeling of freshness.

In addition, they prove to be compatible with a homogeneous dispersion of large amounts of fillers and/or pigments. The compositions according to the invention can thus comprise up to 10% by weight, indeed even at least 15% by weight and in particular at least 20% by weight of pulverulent phase.

Advantageously, the compositions according to the invention can additionally be devoid of gelling agent for oil and/or water or can comprise only a very small amount thereof, for example less than 2% by weight.

Within the meaning of the present invention, the term "fluid" is understood to characterise an ability of the composition to flow under its own weight and in particular to spread when it is deposited on a flat surface.

Advantageously, a composition according to the invention can have a viscosity, measured at 25° C. at a shear rate of 200 min$^{-1}$ (200 revolutions per minute, i.e. a frequency of 50 Hz), ranging from 0.2 to 2 Pa.s (2 to 20 poises), in particular varying from 0.3 to 1 Pa.s (3 to 10 poises) and preferably ranging from 0.4 to 0.8 Pa.s (4 to 8 poises). Such a viscosity makes it possible to easily apply the emulsion and to obtain a homogeneous, uniform and mark-free make-up. The viscosity is measured at 25° C. with a Contraves type TV viscometer equipped with a No. 2 spindle, the measurement being carried out after rotating the spindle for 10 minutes (time at the end of which the viscosity and the rotational speed of the spindle are observed to be stable), at a shear rate of 200 min$^{-1}$.

Dimethicone Copolyol

The dimethicone copolyol employed according to the invention is an oxypropylenated and/or oxyethylenated polydimethyl(methyl)siloxane.

Use may be made, as dimethicone copolyol, of those corresponding to the following formula (II):

$$R_1-SiO-\left[SiO\right]_{\overline{A}}-\left[SiO\right]_{\overline{B}}-Si-R_3 \quad (II)$$

(with $CH_3$ groups and $R_2$ substituents as shown)

in which:
$R_1$, $R_2$ and $R_3$ represent, independently of one another, a $C_1$-$C_6$ alkyl radical or a —$(CH_2)_x$—$(OCH_2CH_2)_y$—$(OCH_2CH_2)_z$—$OR_4$ radical, at least one $R_1$, $R_2$ or $R_3$ radical not being an alkyl radical; $R_4$ being a hydrogen, a $C_1$-$C_3$ alkyl radical or a $C_2$-$C_4$ acyl radical;
A is an integer ranging from 0 to 200;
B is an integer ranging from 0 to 50; provided that A and B are not equal to zero at the same time;
x is an integer ranging from 1 to 6;
y is an integer ranging from 1 to 30;
z is an integer ranging from 0 to 5.

According to a preferred embodiment of the invention, in the compound of formula (II), $R_1$=$R_3$=methyl radical, x is an integer ranging from 2 to 6 and y is an integer ranging from 4 to 30. $R_4$ is in particular a hydrogen.

Mention may be made, as examples of compounds of formula (II), of the compounds of formula (III):

$$(CH_3)_3SiO-[(CH_3)_2SiO]_A-(CH_3SiO)_B-Si(CH_3)_3 \quad (III)$$
$$|$$
$$(CH_2)_2-(OCH_2CH_2)_y-OH$$

in which A is an integer ranging from 20 to 105, B is an integer ranging from 2 to 10 and y is an integer ranging from 10 to 20.

Mention may also be made, as examples of silicone compounds of formula (II), of the compounds of formula (IV):

$$HO-(CH_2CH_2O)_y-(CH_2)_3-[(CH_3)_2SiO]_{A'}-(CH_3)_2 Si-(CH_2)_3-(OCH_2CH_2)_y-OH \quad (IV)$$

in which A' and y are integers ranging from 10 to 20.

Use may be made, as dimethicone copolyol, of those sold under the names DC 5329, DC 7439-146, DC2-5695 and Q4-3667 by Dow Corning; and KF-6013, KF-6015, KF-6016, KF-6017 and KF-6028 by Shin-Etsu.

The compounds DC 5329, DC 7439-146 and DC2-5695 are compounds of formula (III) where, respectively, A is 22, B is 2 and y is 12; A is 103, B is 10 and y is 12; and A is 27, B is 3 and y is 12.

The dimethicone copolyol can be present in the emulsion according to the invention in a content ranging from 1% to 6% by weight, with respect to the total weight of the emulsion, preferably ranging from 1.5% to 4% by weight and preferentially ranging from 2% to 3% by weight.

According to a particular embodiment of the invention, a composition may comprise a weight ratio of dimethicone copolyol/aqueous phase ranging form 0.01 to 0.1.

Preferably, a composition of the invention may comprise a weight ratio dimethicone copolyol/aqueous phase ranging from 0.02 to 0.05.

According to a preferred alternative embodiment of the invention, the abovementioned dimethicone copolyol can be combined with at least one α,ω-substituted oxyalkylenated silicone.

α,ω-Substituted Oxyalkylenated Silicone

In everything which follows or which precedes, the term "silicone" is understood to denote, in conformity with what is generally accepted, any organosilicon polymer or oligomer with a branched or crosslinked and linear or cyclic structure of variable molecular weight obtained by polymerisation and/or polycondensation of suitably functionalised silanes and essentially composed of a repetition of main units in which the silicon atoms are connected to one another via oxygen atoms (siloxane bond =Si—O—Si=), optionally substituted hydrocarbon radicals being directly bonded via a carbon atom to the said silicon atoms. The commonest hydrocarbon radicals are alkyl radicals, in particular $C_1$-$C_{10}$ alkyl radicals and especially methyl radicals, fluoroalkyl radicals and aryl radicals, in particular phenyl radicals. They can, for example, be substituted by $C_1$-$C_{40}$ ester or ether groups or $C_7$-$C_{60}$ aralkyl groups.

Thus, the α,ω-substituted oxyalkylene silicone which can be used according to the invention is an organosilicon polymer as defined above with a linear structure which is substituted at the two ends of the main chain by oxyalkylene groups connected to the Si atoms via a hydrocarbon group.

Preferably, the α,ω-substituted oxyalkylenated silicone corresponds to the following general formula (I):

$$R-Si(R_2)_2-O-\left[Si(R_2)_2-O\right]_m-Si(R_2)_2-R \quad (I)$$

in which: $R=-(CH_2)_pO-(C_2H_4O)_x(C_3H_6O)_yR^1$
where: $R^1$ represents H, $CH_3$ or $CH_2CH_3$,
p is an integer ranging from 1 to 5, x varies from 1 to 100 and y varies from 0 to 50,
it being possible for the $(C_2H_4O)$ and $(C_3H_6O)$ units to be distributed randomly or in blocks,
the $R^2$ radicals represent a $C_1$-$C_3$ alkyl radical or a phenyl radical,
$5 \leq m \leq 300$.

Preferably, the α,ω-substituted oxyalkylenated silicone used according to the present invention corresponds to the general formula (I) for which only the $R^2$ radicals are methyl radicals and:
p ranges from 2 to 4,
x ranges from 3 to 100,
m ranges from 50 to 200.

Preferably again, the average molecular weight of R ranges from 800 to 2600.

Preferably, the ratio by weight of the $C_2H_4O$ units with respect to the $C_3H_6O$ units ranges from 100:10 to 20:80. Advantageously, this ratio is approximately 42/58.

Preferably again, $R^1$ is the methyl group.

More preferably still, the emulsion according to the invention comprises the α,ω-oxyalkylenated silicone of following formula:

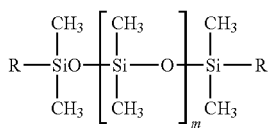

in which:

m=100,

R=$(CH_2)_3$—O—$(C_2H_4O)_x$—$(C_3H_6O)_y$—$CH_3$, where x ranges from 3 to 100 and y ranges from 1 to 50, the ratio by weight of the number of $C_2H_4O$ to the number of $C_3H_6O$ being approximately 42/58 and the average molecular weight of R ranging from 800 to 1000.

The α,ω-substituted oxyalkylenated silicone as defined above can be used according to the invention in a proportion ranging from 0.5 to 5% by weight, in particular from 1 to 4% by weight and more particularly from 2 to 3% by weight, with respect to the total weight of the composition.

Mention may in particular be made, among the commercial products which may comprise all or part of the α,ω-substituted oxyalkylenated silicones which can be used according to the invention as emulsifier, of those sold under the names of "Abil EM 97" by Goldschmidt or also of "KF 6009", "X22-4350", "X22-4349" or "KF 6008" by Shin Etsu.

In particular, the product can be cetyl dimethicone copolyol.

Polyoxyalkylenated Silicone

According to another alternative embodiment of the invention, the dimethicone copolyol required according to the invention can be used in combination with at least one oxyalkylenated silicone.

The polyoxyalkylenated silicone elastomer is a crosslinked organopolysiloxane which can be obtained by a crosslinking addition reaction of a diorganopolysiloxane comprising at least one hydrogen bonded to silicon and of a polyoxyalkylene having at least two groups comprising ethylenic unsaturation.

Preferably, the polyoxyalkylenated crosslinked organopolysiloxane is obtained by a crosslinking addition reaction (A1) of a diorganopolysiloxane comprising at least two hydrogens each bonded to a silicon and (B1) of a polyoxyalkylene having at least two groups possessing ethylenic unsaturation, in particular in the presence (C1) of a platinum catalyst, such as, for example, described in U.S. Pat. No. 5,236,986 and U.S. Pat. No. 5,412,004.

In particular, the organopolysiloxane can be obtained by reaction of a polyoxyalkylene (in particular a polyoxyethylene and/or polyoxypropylene) possessing dimethylvinylsiloxy ends and of a methylhydropolysiloxane possessing trimethylsiloxy ends, in the presence of a platinum catalyst.

The organic groups bonded to the silicon atoms of the compound (A1) can be alkyl groups having from 1 to 18 carbon atoms, such as methyl, ethyl, propyl, butyl, octyl, decyl, dodecyl (or lauryl), myristyl, cetyl or stearyl; substituted alkyl groups, such as 2-phenylethyl, 2-phenylpropyl or 3,3,3-trifluoropropyl; aryl groups, such as phenyl, tolyl or xylyl; substituted aryl groups, such as phenylethyl; and substituted monovalent hydrocarbon groups, such as an epoxy group, a carboxylate ester group or a mercapto group.

The compound (A1) can thus be chosen from methylhydropolysiloxanes possessing trimethylsiloxy ends, dimethylsiloxane/methylhydrosiloxane copolymers possessing trimethylsiloxy ends, cyclic dimethylsiloxane/methylhydrosiloxane copolymers, or dimethylsiloxane/methylhydrosiloxane/laurylmethylsiloxane copolymers possessing trimethylsiloxy ends.

The compound (C1) is the catalyst of the crosslinking reaction and is in particular chloroplatinic acid, chloroplatinic acid/olefin complexes, chloroplatinic acid/alkenylsiloxane complexes, chloroplatinic acid/diketone complexes, platinum black and platinum-on-support.

Advantageously, the polyalkylenated silicone elastomers can be formed from divinyl compounds, in particular polyoxyalkylenes having at least two vinyl groups, which react with Si—H bonds of a polysiloxane.

The polyoxyalkylenated silicone elastomer according to the invention is preferably mixed with at least one hydrocarbon oil and/or one silicone oil in order to form a gel. In these gels, the polyoxyalkylenated elastomer is in the form of nonspherical particles.

Polyoxyalkylenated elastomers are described in particular in U.S. Pat. No. 5,236,986, U.S. Pat. No. 5,412,004, U.S. Pat. No. 5,837,793 and U.S. Pat. No. 5,811,487, the contents of which are incorporated by reference.

Use can be made, as polyoxyalkylenated silicone elastomer, of those sold under the names "KSG-21", "KSG-20", "KSG-30", "KSG-31", KSG-32", "KSG-33", "KSG-210", "KSG-310", "KSG-320", "KSG-330", "KSG-340" and "X-226146" by Shin Etsu and "DC9010" and "DC9011" by Dow Corning.

The emulsifying silicone elastomer can also be chosen from polyglycerolated silicone elastomers.

The polyglycerolated silicone elastomer is a crosslinked organopolysiloxane elastomer which can be obtained by a crosslinking addition reaction of a diorganopolysiloxane comprising at least one hydrogen bonded to silicon and of polyglycerolated compounds having groups possessing ethylenic unsaturation, in particular in the presence of a platinum catalyst.

Preferably, the crosslinked organopolysiloxane elastomers obtained by a crosslinking addition reaction (A) of a diorganopolysiloxane comprising at least two hydrogens each bonded to a silicon and (B) of glycerolated compounds having at least two groups possessing ethylenic unsaturation, in particular in the presence (C) of a platinum catalyst.

In particular, the organopolysiloxane can be obtained by reaction of a polyglycerolated compound possessing dimethylvinylsiloxy ends and of a methylhydropolysiloxane possessing trimethylsiloxy ends, in the presence of a platinum catalyst.

The compound (A) is the base reactant for the formation of an organopolysiloxane elastomer and the crosslinking takes place by an addition reaction of the compound (A) with the compound (B) in the presence of the catalyst (C).

The compound (A) is in particular an organopolysiloxane having at least 2 hydrogen atoms bonded to separate silicon atoms in each molecule.

The compound (A) can exhibit any molecular structure, in particular a linear chain or branched chain structure or a cyclic structure.

The compound (A) can have a viscosity of 25° C. ranging from 1 to 50 000 centistokes, in particular in order to be satisfactorily miscible with the compound (B).

The organic groups bonded to the silicon atoms of the compound (A) can be alkyl groups having from 1 to 18 carbon atoms, such as methyl, ethyl, propyl, butyl, octyl, decyl, dodecyl (or lauryl), myristyl, cetyl or stearyl; substituted alkyl groups, such as 2-phenylethyl, 2-phenylpropyl or 3,3,3-trifluoropropyl; aryl groups, such as phenyl, tolyl or xylyl; substituted aryl groups, such as phenylethyl; and substituted monovalent hydrocarbon groups, such as an epoxy group, a carboxylate ester group or a mercapto group. Preferably, the said organic group is chosen from the methyl, phenyl and lauryl groups.

The compound (A) can thus be chosen from methylhydropolysiloxanes possessing trimethylsiloxy ends, dimethylsiloxane/methylhydrosiloxane copolymers possessing trimethylsiloxy ends, cyclic dimethylsiloxane/methylhydrosiloxane copolymers, or dimethylsiloxane/methylhydrosiloxane/laurylmethylsiloxane copolymers possessing trimethylsiloxy ends.

The compound (B) can be a polyglycerolated compound corresponding to the following formula (B'):

 (B')

in which m is an integer ranging from 2 to 6, n is an integer ranging from 2 to 200, preferably ranging from 2 to 100, preferably ranging from 2 to 50, preferably ranging from 2 to 20, preferably ranging from 2 to 10 and preferentially ranging from 2 to 5 and in particular equal to 3; Gly denotes:

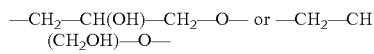

Advantageously, the sum of the number of ethylene groups per molecule of the compound (B) and of the number of hydrogen atoms bonded to silicon atoms per molecule of the compound (A) is at least 4.

It is advantageous for the compound (A) to be added in an amount such that the molecular ratio of the total amount of hydrogen atoms bonded to silicon atoms in the compound (A) to the total amount of all the groups possessing ethylenic unsaturation in the compound (B) is within the range from 1/1 to 20/1.

The compound (C) is the catalyst of the crosslinking reaction and is in particular chloroplatinic acid, chloroplatinic acid/olefin complexes, chloroplatinic acid/alkenylsiloxane complexes, chloroplatinic acid/diketone complexes, platinum black and platinum-on-support.

The catalyst (C) is preferably added from 0.1 to 1000 parts by weight, better still from 1 to 100 parts by weight, as platinum metal proper, per 1000 parts by weight of the total amount of the compounds (A) and (B).

The polyglycerolated silicone elastomer according to the invention is generally mixed with at least one hydrocarbon oil and/or one silicone oil in order to form a gel. In these gels, the polyglycerolated elastomer is often in the form of nonspherical particles.

Such elastomers are described in particular in Patent Application WO 2004/024798.

Use may be made, as polyglycerolated silicone elastomers, of those sold under the names "KSG-710", "KSG-810", "KSG-820", "KSG-830" and "KSG-840" by Shin Etsu.

According to one aspect of the invention, these silicone elastomers can be present in the composition according to the invention in a total content at least greater than 3% by weight, with respect to the total weight of the composition, in particular ranging from 3 to 15% by weight, preferably greater than or equal to 3.5% by weight, in particular ranging from 3.5 to 10% by weight, and more preferably greater than or equal to 4% by weight, in particular ranging from 4 to 7% by weight.

Lower $C_2$ to $C_8$ Monoalcohol

The lower monoalcohols more particularly suitable for the invention comprise from 2 to 8 carbon atoms, in particular from 2 to 6 carbon atoms and especially from 2 to 4 carbon atoms, such as ethanol, isopropanol, propanol or butanol.

Ethanol and isopropanol and preferably ethanol are also very particularly suitable for the invention.

As specified above, this alcohol is present in a proportion of at least 5% by weight, in particular of at least 7% by weight, especially in a proportion of at least 10% by weight and more particularly in a proportion of at least 15% by weight of the composition.

For reasons of comfort, it will be favourable to have less than 40% by weight and in particular less than 30% by weight of monoalcohol in the compositions according to the invention.

Thus, the monoalcohol can represent at least 15% by weight, and even 20% by weight and up to 40% by weight of the aqueous phase.

Aqueous Phase

As specified above, the aqueous phase forms at least 40% by weight, in particular at least 45% by weight, indeed even more than 50% by weight and especially more than 60% by weight of the total weight of the composition according to the invention.

In addition to the lower monoalcohol(s) defined above, this aqueous phase can comprise other alcohol(s), in particular polyethylene glycols having from 6 to 80 ethylene oxide units; polyols, such as propylene glycol, isoprene glycol, butylene glycol, glycerol, sorbitol, glycols, such as propylene glycol, butylene glycol, dipropylene glycol or diethylene glycol, glycol ethers, such as mono-, di- or tripropylene glycol or mono-, di- or triethylene glycol ($C_1$-$C_4$)alkyl ether, and their mixtures.

The aqueous phase comprises water. The water can be a floral water, such as cornflower water, and/or a mineral water, such as water from Vittel, water from Lucas or water from La Roche-Posay, and/or a thermal water.

According to a particular embodiment of the invention, the amount of water in the aqueous phase is higher than the total amount of alcohols/polyols in said aqueous phase.

In particular, the amount of polyols in the composition may represent from 0 to 25% by weight, preferably from 1 to 15% by weight, and more preferably from 2 to 8% by weight relative to the total weight of the composition.

The aqueous phase can additionally comprise stabilising agents, for example sodium chloride, magnesium dichloride and magnesium sulphate.

The aqueous phase can also comprise any water-soluble or water-dispersible compound compatible with an aqueous phase, such as gelling agents, film-forming polymers, thickeners, surfactants and their mixtures.

Preferably, the aqueous phase is present in the emulsion according to the invention in a content ranging from 45% to 70%, preferably ranging from 50% to 60% by weight, with respect to the total weight of the emulsion.

Fatty Phase

The term "volatile oil" is understood to mean an oil (or nonaqueous medium) capable of evaporating on contact with the skin in less than one hour at ambient temperature and atmospheric pressure. The volatile oil is a volatile cosmetic oil which is liquid at ambient temperature and which has in particular a nonzero vapour pressure at ambient temperature and atmospheric pressure, in particular which has a vapour pressure ranging from 0.13 Pa to 40 000 Pa ($10^{-3}$ to 300 mmHg), preferably ranging from 1.3 Pa to 13 000 Pa (0.01 to 100 mmHg), and preferentially ranging from 1.3 Pa to 1300 Pa (0.01 to 10 mmHg).

In addition, the volatile oil generally has a boiling point, measured at atmospheric pressure, ranging from 150° C. to 260° C. and preferably ranging from 170° C. to 250° C.

Advantageously, the fatty phase comprises from 15% to 40% by weight, preferably ranging from 20% to 35% by weight and preferentially ranging from 17% to 26% by weight of volatile oil(s), with respect to the total weight of the composition.

The term "hydrocarbon oil" is understood to mean an oil essentially formed, and even composed, of carbon and hydrogen atoms and optionally of oxygen and nitrogen atoms which does not comprise a silicon or fluorine atom; it can comprise ester, ether, amine and amide groups.

The term "silicone oil" is understood to mean an oil comprising at least one silicon atom and in particular comprising Si-0 groups.

The term "fluorinated oil" is understood to mean an oil comprising at least one fluorine atom.

The volatile hydrocarbon oil which can be used in the invention can be chosen from hydrocarbon oils having a flash point ranging from 40° C. to 102° C., preferably ranging from 40° C. to 55° C., and preferably ranging from 40° C. to 50° C.

Mention may be made, as volatile hydrocarbon oil, of volatile hydrocarbon oils having from 8 to 16 carbon atoms and their mixtures, in particular branched $C_8$-$C_{16}$ alkanes, such as $C_8$-$C_{16}$ isoalkanes (also known as isoparaffins), isododecane, isodecane, isohexadecane and, for example, the oils sold under the Isopar or Permethyl commercial names, branched $C_8$-$C_{16}$ esters, such as isohexyl neopentanoate, and their mixtures. Preferably, the volatile hydrocarbon oil is chosen from volatile hydrocarbon oils having from 8 to 16 carbon atoms and their mixtures, in particular from isododecane, isodecane or isohexadecane, and is in particular isododecane.

The volatile hydrocarbon oil can be present in a content ranging from 6% to 25% by weight, with respect to the total weight of the emulsion, preferably ranging from 10% to 20% by weight and preferentially ranging from 10% to 15% by weight. In particular, the composition comprises at least 10% by weight, with respect to the total weight of the emulsion, of volatile hydrocarbon oil.

The volatile silicone oil which can be used in the invention can be chosen from silicon oils having a flash point ranging from 40° C. to 102° C., preferably having a flash point of greater than 55° C. and less than or equal to 95° C., and preferentially ranging from 65° C. to 95° C.

Mention may be made, as volatile silicone oil, of linear or cyclic silicone oils having from 2 to 7 silicon atoms, these silicones optionally comprising alkyl or alkoxy groups having from 1 to 10 carbon atoms. Mention may in particular be made, as examples of volatile silicone oil, of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane and their mixtures.

Mention may be made, as volatile fluorinated oil, of nonafluoroethoxybutane, nonafluoromethoxybutane, decafluoropentane, tetradecafluorohexane, dodecafluoropentane and their mixtures.

The volatile oil chosen from volatile silicone oils, volatile fluorinated oils and their mixtures can be present in a content ranging from 20% to 32% by weight, with respect to the total weight of the emulsion, preferably ranging from 20% to 30% by weight and preferentially ranging from 22% to 26% by weight, with respect to the total weight of the composition.

The fatty phase of the emulsion according to the invention can additionally comprise at least one non-volatile oil.

This oil or one of its mixtures can be present in a content ranging from 0.1% to 12% by weight, with respect to the total weight of the emulsion, and preferably ranging from 1% to 5% by weight.

The emulsion advantageously comprises from 15% to 40% by weight, with respect to the total weight of the emulsion, of oils and preferably from 20% to 35% by weight.

According to a particular embodiment of the invention, the composition may comprise a weight ratio of aqueous phase/oil phase ranging from 1 to 5.

Preferably, a composition may comprise a weight ratio of aqueous phase/oil phase ranging from 1.5 to 4.

More preferably, a composition may comprise a weight ratio of aqueous phase/oil phase ranging from 1.8 to 3.

The non-volatile oil can be chosen from carbon-comprising, hydrocarbon-comprising and/or silicone oils of mineral, animal, vegetable or synthetic origin, and their mixtures, insofar as they are compatible with the use envisaged.

Mention may be made of non-volatile hydrocarbon oils, such as liquid paraffin or liquid petrolatum, isoeicosane, mink, turtle or soybean oil, perhydrosqualene, sweet almond, calophyllum, palm, grape seed, sesame, corn, arara, rapeseed, sunflower, cottonseed, apricot, castor, avocado, jojoba, olive or cereal germ oil; esters of lanolic acid, oleic acid, lauric acid or stearic acid; fatty esters, such as isopropyl myristate, isopropyl palmitate, butyl stearate, hexyl laurate, diisopropyl adipate, isononyl isononanoate, 2-ethylhexyl palmitate, 2-hexyldexyl laurate, 2-octyldecyl palmitate, 2-octyldodecyl myristate or lactate, di(2-ethylhexyl) succinate, diisostearyl malate, glyceryl triisostearate or diglyceryl triisostearate; higher fatty acids, such as myristic acid, palmitic acid, stearic acid, behenic acid, oleic acid, linoleic acid, linolenic acid or isostearic acid; or higher fatty alcohols, such as cetanol, stearyl alcohol or oleyl alcohol, linoleyl or linolenyl alcohol, isostearyl alcohol or octyldodecanol.

Mention may be made, as non-volatile silicone oil, of polydimethylsiloxanes (PDMSs), which are optionally phenylated, such as phenyl trimethicones, or optionally substituted by aliphatic and/or aromatic groups or by functional groups, such as hydroxyl, thiol and/or amine groups; polysiloxanes modified with fatty acids, fatty alcohols or polyoxyalkylenes, and their mixtures.

The fatty phase can also comprise at least one wax, at least one gum and/or at least one pasty fatty substance of vegetable, animal, mineral or synthetic origin, indeed even silicone origin, and their mixtures.

Mention may be made among waxes which are solid at ambient temperature and which are capable of being present in the composition according to the invention, of hydrocarbon waxes, such as beeswax, carnauba, candelilla, ouricury or Japan wax, cork fibre or sugarcane waxes, paraffin or lignite waxes, microcrystalline waxes, lanolin wax, montan wax, ozokerites, polyethylene waxes, the waxes obtained by the Fischer-Tropsch synthesis, hydrogenated oils, fatty esters and glycerides which are solid at 25° C. Use may also be made of silicone waxes, among which may be mentioned alkylpolymethylsiloxanes, alkoxypolymethylsiloxanes and/or polymethylsiloxane esters. The waxes can be provided in the form of stable dispersions of colloidal wax particles such that they can be prepared according to known methods, such as those of "Microemulsions Theory and Practice", edited by L. M. Prince, Academic Press (1977), pages 21-32. Mention may be made, as wax which is liquid at ambient temperature, of jojoba oil.

The waxes can be present in a proportion of 0.1% to 10% by weight, with respect to the total weight of the emulsion, and preferably of 0.1 to 5% by weight.

The pasty fatty compounds can be defined using at least one of the following physicochemical properties:
- a viscosity of 0.1 to 40 Pa.s (1 to 400 poises), preferably 0.5 to 25 Pa.s, measured at 40° C. with a Contraves TV rotary viscometer equipped with an MS-r 3 or MS-r4 spindle at a frequency of 60 Hz,
- a melting point of 25-70° C., preferably 25-55° C.

The compositions of the invention can also comprise at least one alkyl, alkoxy or phenyl dimethicone, such as, for example, the product sold under the name of "Abil Wax 2440" by Goldschmidt.

The emulsion according to the invention can additionally comprise a thickening agent for the fatty phase. The thickening agent can be chosen from:
- organomodified clays, which are clays treated with compounds chosen in particular from quaternary amines or tertiary amines. Mention may be made, as organomodified clays, of organomodified bentonites, such as those sold under the name "Bentone 34" by Rheox, or organomodified hectorites, such as those sold under the name "Bentone 27" or "Bentone 38" by Rheox.
- hydrophobic pyrogenic silica. Such silicas are sold, for example, under the references "Aerosil R812®" by Degussa and "Cab-O-Sil TS-530®" by Cabot and under the references "Aerosil R972®" and "Aerosil R974®" by Degussa and "Cab-O-Sil TS-610®" and "Cab-O-Sil TS-720®" by Cabot.

The thickening agent for the fatty phase can be present in a content ranging from 0.1% to 5% by weight, with respect to the total emulsion, and better still from 0.4% to 3% by weight.

The fatty phase can represent from 30% to 45% by weight, preferably from 35% to 45% by weight, with respect to the total weight of the emulsion.

In a known way, all the compositions of the invention can comprise one or more of the adjuvants usual in the cosmetic and dermatological fields: hydrophilic or lipophilic gelling and/or thickening agents; fillers; moisturising agents; emollients; hydrophilic or lipophilic active principles; agents for combating free radicals; sequestering agents; antioxidants; preservatives; basifying or acidifying agents; fragrances; film-forming agents; colouring materials; and their mixtures. The amounts of these various adjuvants are those conventionally used in foundations.

As specified above, the compositions according to the invention can advantageously, and contrary to all expectation, comprise more than 10% by weight, in particular more than 15% by weight, indeed more than 20% by weight, of a pulverulent phase. The latter is dispersed therein in a homogeneous and stabilised form. Within the meaning of the present invention, the term "pulverulent phase" covers all particles of pigment and/or filler type, as defined below.

The fillers can be present in the emulsion in a content ranging from 0.1% to 10% by weight, with respect to the total weight of the emulsion, preferably 0.1% to 7% by weight. Mention may in particular be made of talc, mica, silica, kaolin, starch, boron nitride, calcium carbonate, magnesium carbonate, basic magnesium carbonate, microcrystalline cellulose, powders formed of synthetic polymers, such as polyethylene, polyesters, polyamides, such as those sold under the "Nylon" tradename, or polytetrafluoroethylene ("Teflon"), and silicone powders.

As regards the colouring materials, they can be water-soluble colouring materials of vegetable, mineral or synthetic origin, pigments and pearlescent agents.

Advantageously, the pigments can be present in a hydrophobic coated form in the emulsion according to the invention. They can more particularly be pigments treated at the surface with a hydrophobic agent in order to render them compatible with the fatty phase of the emulsion, in particular in order for them to have good wettability with the oils of the fatty phase. Thus, these treated pigments are well dispersed in the fatty phase.

The pigments intended to be coated can be inorganic or organic pigments. Use may be made, as pigments, of metal oxides, such as iron oxides, in particular those which are yellow, red, brown or black in colour, titanium dioxides, cerium oxide, zirconium oxide or chromium oxide; manganese violet, ultramarine blue, Prussian blue, ferric blue, bismuth oxychloride, mother-of-pearl, mica covered with titanium oxide or with bismuth oxychloride, coloured pearlescent pigments, such as titanium oxide-coated mica with iron oxides, titanium oxide-coated mica with in particular ferric blue or chromium oxide, or titanium oxide-coated mica with an organic pigment of the abovementioned type, and also pearlescent pigments based on bismuth oxychloride, and their mixtures.

Use is preferably made of pigments formed of iron oxides or titanium oxide.

The hydrophobic treating agent can be chosen from silicones, such as methicones, dimethicones or perfluoroalkylsilanes; fatty acids, such as stearic acid; metal soaps, such as aluminium dimyristate or the aluminium salt of hydrogenated tallow glutamate, perfluoroalkyl phosphates, perfluoroalkylsilanes, perfluoroalkylsilazanes, poly(hexafluoropropylene oxide)s, polyorganosiloxanes comprising perfluoroalkyl or perfluoropolyether groups, amino acids; N-acylated amino acids or their salts; lecithin, isopropyl triisostearyl titanate, and their mixtures.

The N-acylated amino acids can comprise an acyl group having from 8 to 22 carbon atoms, such as, for example, a 2-ethylhexanoyl, caproyl, lauroyl, myristoyl, palmitoyl, stearoyl or cocoyl group. The salts of these compounds can be aluminium, magnesium, calcium, zirconium, zinc, sodium or potassium salts. The amino acid can, for example, be lysine, glutamic acid or alanine.

The term "alkyl" mentioned in the abovementioned compounds denotes in particular an alkyl group having from 1 to 30 carbon atoms, preferably having from 5 to 16 carbon atoms.

Hydrophobic treated pigments are described in particular in Application EP-A-1 086 683.

The hydrophobic coated pigments can be present in a content ranging from 0.5% to 20 by weight, with respect to the total weight of the composition, preferably in a content at least equal to 5% by weight, in particular ranging from 5% to 20% by weight (in particular ranging from 8% to 20% by weight), and preferentially ranging from 8% to 15% by weight.

Likewise, the compositions according to the invention can comprise active principles.

Mention may be made, as active principles which can be used in the composition of the invention, for example, of moisturising agents, such as protein hydrolysates, and polyols, for example glycerol, glycols, for example polyethylene glycols, and sugar derivatives; natural extracts; antiinflammatories; procyanidol oligomers; vitamins, such as vitamin A (retinol), vitamin E (tocopherol), vitamin C (ascorbic acid), vitamin B5 (panthenol), vitamin B3 (niacinamide), the derivatives of these vitamins (in particular esters) and their mixtures; urea; caffeine; salicylic acid and its derivatives; alpha-hydroxy acids, such as lactic acid and glycolic acid, and their derivatives; retinoids, such as carotenoid and vitamin A derivatives; sunscreen; hydrocortisone; melatonin; algal, fungal, plant, yeast or bacterial extracts; enzymes; steroids; antibacterial active principles, such as 2,4,4'-trichloro-2'-hydroxydiphenyl ether (or triclosan), 3,4,4'-trichlorocarbanilide (or triclocarban) and the acids indicated above and in particular salicylic acid and its derivatives; tightening agents; and their mixtures.

The sunscreens (or UV screening agents) can be chosen from organic screening agents, physical screening agents and their mixtures.

The composition of the invention can comprise, as chemical sunscreens which can be used in the composition of the invention, any UV-A or UV-B screening agent which can be used in the cosmetics field.

Of course, a person skilled in the art will take care to choose the optional adjuvants added to the composition according to the invention so that the advantageous properties intrinsically attached to the composition according to the invention are not, or not substantially, detrimentally affected by the envisaged addition.

The invention is illustrated in more detail in the following examples.

EXAMPLE 1

A foundation in the form of a water-in-oil emulsion is prepared from the following composition:

| Chemical name | Amount in weight |
|---|---|
| Magnesium sulphate heptahydrate | 0.70 |
| Talc: Micronised magnesium silicate (particle size: 5 microns) Micro Ace P3 from Nippon Talc | 0.50 |
| Refined plant perhydrosqualene | 1.00 |
| Anatase titanium oxide coated with aluminium stearoylglutamate (97/3) NAI-TAO-77891 from Miyoshi Kasei | 8.23 |
| Red iron oxide coated with aluminium stearoylglutamate (3%) NAI-C33-8001-10 from Miyoshi Kasei | 0.25 |
| Black iron oxide coated with aluminium stearoylglutamate (3%) NAI-C33-7001-10 from Miyoshi Kasei | 0.13 |
| Yellow iron oxide coated with aluminium stearoylglutamate (3%) NAI-C33-9001-10 from Miyoshi Kasei | 1.39 |
| Stabilised 2-ethylhexyl 4-methoxycinnamate (0.1% BHT) | 3.00 |
| Nylon 12 powder Orgasol 2002 EXD NAT COS from Arkema | 0.50 |
| Cyclopentadimethylsiloxane | 23.65 |
| Phenyl trimethylsiloxy trisiloxane (viscosity: 20 cSt-MW: 372) | 2.00 |
| Polydimethylsiloxane possessing α-ω oxyethylene/oxypropylene groups in solution in cyclopentasiloxane Abil EM 97 from Goldschmidt | 1.00 |
| Oxyethylenated polydimethylsiloxane (DP: 70-viscosity: 500 cSt) KF 6017 from Shin-Etsu | 2.00 |
| 1,3-Butylene glycol | 3.00 |
| Undenatured 96° ethyl alcohol | 11.00 |
| Microbiologically clean deionised water | q.s. for 100 |

The emulsion is prepared at ambient temperature, on the one hand by mixing the pigments in a portion of the cyclopentasiloxane, on the other hand by mixing the other oils with the surfactants, and then the mixture of pigments and the nylon are added to the other mixed constituents of the fatty phase. The mixture of the constituents of the aqueous phase is subsequently prepared and is poured into the mixture of the fatty phase, with stirring according to known means, in order to obtain the emulsion at the end.

This foundation is stable after storing at ambient temperature (25° C.) for 4 months. It is easy to apply to the skin with a good sensation of smoothness and softness, and very good slip; it quickly dries after application of the product and the make-up obtained is very homogeneous in colour, without leaving marks on the skin.

Two other foundation formulations were prepared on the basis of the preceding formulation by respectively employing 15% by weight and 20% by weight of alcohol, the amounts of water having been adjusted in consequence.

The three formulations thus obtained prove to possess the properties expected in terms of fluidity and stability. No phenomenon of phase separation between the oily phase and the aqueous phase is recorded.

What is more, the three formulations provide a feeling of freshness on application.

EXAMPLE 2

Three foundations A, B and C are prepared according to the protocol described in Example 1, these three foundations having the following compositions:

| Chemical name | A | B | C |
|---|---|---|---|
| Sodium chloride | 0.70 | 0.70 | 0.70 |
| Smectite: Modified magnesium silicate in cyclopentadimethylsiloxane and ethanol (18/77/5) Bentone Gel VS 5 from Elementis | 3.00 | — | — |
| Smectite: Modified magnesium silicate in isododecane Bentone Gel ISD V from Elementis | — | 1.50 | 1.50 |
| Anatase titanium oxide coated with aluminium stearoylglutamate (97/3) NAI-TAO-77891 from Miyoshi Kasei | 7.68 | 9.21 | 9.21 |
| Red iron oxide coated with aluminium stearoylglutamate (3%) NAI-C33-8001-10 from Miyoshi Kasei | 0.33 | 0.40 | 0.40 |
| Black iron oxide coated with aluminium stearoylglutamate (3%) NAI-C33-7001-10 from Miyoshi Kasei | 0.19 | 0.23 | 0.23 |

-continued

| Chemical name | A | B | C |
|---|---|---|---|
| Yellow iron oxide coated with aluminium stearoyl-glutamate (3%) NAI-C33-9001-10 from Miyoshi Kasei | 1.80 | 2.16 | 2.16 |
| Silica-titanium oxide-mica-tin oxide (35/40.5/24/0.5)(size of the particles 10-60 μm) Xirona Volcanic Fire from Merck | 2.00 | — | 1.00 |
| Bismuth oxychloride and ethylhexyl hydroxystearate Biron Liquid Silver from Merck | — | 1.00 | — |
| Cyclopentadimethylsiloxane (viscosity: 5 cSt) Dow Corning 245 Fluid from Dow Corning | 18.60 | — | — |
| Polydimethylsiloxane (viscosity: 5 cSt) Dow Corning Fluid 200 5 cS from Dow Corning | 15.00 | 7.00 | 7.00 |
| Oxyethylenated polydimethylsiloxane (DP: 70-viscosity: 500 cSt) KF 6017 from Shin-Etsu | 5.00 | 5.00 | 5.00 |
| 1,3-Butylene glycol | 3.00 | 5.00 | 5.00 |
| Undenatured 96° ethyl alcohol | 5.00 | 10.00 | 20.00 |
| Microbiologically clean deionised water | q.s. for 100 | q.s. for 100 | q.s. for 100 |
| Isododecane | — | 17.20 | 17.20 |
| Propylene glycol | 3.00 | 2.00 | 2.00 |

All the formulations prove to provide properties expected in terms of stability and freshness.

EXAMPLE 3

A foundation is prepared according to the protocol described in Example 1, which foundation has the following formulation:

| Chemical name | |
|---|---|
| Ethylenediaminetetraacetic acid, disodium salt, dihydrate | 0.2 |
| Sodium chloride | 1 |
| Titanium oxide (anatase) coated with perfluoroalkyl phosphate (95/5) (CI: 77891) PF 5 TiO2 100 from Daito Kasei Kogyo | 9.06 |
| Red iron oxide treated with perfluoroalkyl phosphate (95/5) PFX-5 Sunpuro Red C33-8001 from Daito Kaseo Kogyo | 0.27 |
| Black iron oxide treated with perfluoroalkyl phosphate (95/5) PFX-5 Sunpuro Black C33-7001 from Daito Kasei Kogyo | 0.14 |
| Yellow iron oxide treated with perfluoroalkyl phosphate (95/5) PFX-5 Sunpuro Yellow C33-9001 from Daito Kasei Kogyo | 1.53 |
| 2-Phenoxyethanol | 0.4 |
| Methyl p-hydroxybenzoate | 0.2 |
| Stabilised 2-ethylhexyl 4-methoxycinnamate (0.1% BHT) | 3 |
| Cyclopentadimethylsiloxane | 17.6 |
| Polydimethylsiloxane (viscosity: 5 cSt) | 2.5 |
| Oxyethylenated polymethylisostearyldimethylsiloxane (MW: 6000) KF 6028 from Shin-Etsu | 2 |
| Silicone chains crosslinked with polyglycerin KSG 710 from Shin-Etsu | 7 |
| Denatured 96° ethyl alcohol | 7 |
| Microbiologically clean deionised water | q.s. for 100 |
| Glycerol | 5 |

The invention claimed is:

1. A fluid care and/or make-up cosmetic composition for skin, comprising:
   a fatty phase;
   an aqueous phase; and
   at least one dimethicone copolyol;
   wherein
   the fluid composition is a foundation,
   the fluid composition is a water-in-oil emulsion,
   a viscosity, measured at 25° C. at a shear rate of 200 min$^{-1}$, is from 0.3 to 1 Pa.s,
   a content of the aqueous phase is from 40 to 60% by weight, with respect to the total weight of the composition,
   the fluid composition comprises at least 5% by weight, with respect to the total weight of the composition, of at least one $C_2$ to $C_8$ monoalcohol,
   the fluid composition comprises at least 4-0% 20% by weight of a pulverulent phase with respect to the total weight of the composition,
   a weight ratio of dimethicone copolyol to aqueous phase ranges from 0.01 to 0.1, and
   in the fluid composition, the amount of water in the aqueous phase is higher than the total amount of alcohols/polyols in the aqueous phase.

2. The composition according to claim 1, wherein the at least one $C_2$ to $C_8$ monoalcohol is a $C_2$ to $C_6$ monoalcohol.

3. The composition according to claim 1, wherein the monoalcohol is ethanol.

4. The composition according to claim 1, wherein the % by weight of the at least one $C_2$ to $C_8$ monoalcohol is at least 7% by weight.

5. The composition according to claim 1, wherein the content of the aqueous phase is at least 45% by weight.

6. The composition according to claim 1, wherein the at least one dimethicone copolyol is a compound of the following formula (11):

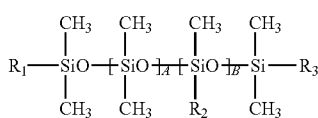
(II)

wherein:

$R_1$, $R_2$ and $R_3$ each represent, independently of one another, a $C_1$-$C_6$ alkyl radical or a —$(CH_2)_x$—$(OCH_2CH_2)_y$—$(OCH_2CH_2CH_2)_z$—$OR_4$ radical, with the proviso that at least one of $R_1$, $R_2$ or $R_3$ radical is not an alkyl radical;

$R_4$ is a hydrogen, a $C_1$-$C_3$ alkyl radical or a $C_2$-$C_4$ acyl radical;

A is an integer from 0 to 200;

B is an integer from 0 to 50; provided that A and B are not equal to zero at the same time;

x is an integer from 1 to 6;

y is an integer from 1 to 30; and z is an integer from 0 to 5.

7. The composition according to claim 6, wherein $R_1$=$R_3$=methyl radical, x is an integer from 2 to 6, and y is an integer from 4 to 30.

8. The composition according to claim 6, wherein $R_4$ is a hydrogen.

9. The composition according to claim 1, wherein the at least one dimethicone copolyol is a compound of the following formula (III):

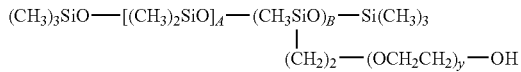
(III)

wherein A is an integer from 20 to 105,

B is an integer from 2 to 10 and y is an integer from 10 to 20.

10. The composition according to claim 1, wherein the at least one dimethicone copolyol is a compound of the following formula (TV):

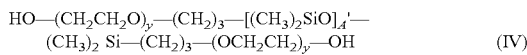
(IV)

wherein

A' and y are each independently, integers from 10 to 20.

11. The composition according to claim 1, wherein a content of the at least one dimethicone copolyol is from 1% to 6% by weight with respect to the total weight of the composition.

12. The composition according to claim 1, further comprising an α,ω-substituted oxyalkylenated silicone.

13. The composition according to claim 12 wherein the at least one dimethicone copolyol is cetyl dimethicone copolyol.

14. The composition according to claim 12, wherein a content of the up-substituted oxyalkylenated silicone is from 0.5% to 5% by weight, with respect to the total weight of the composition.

15. The composition according to claim 1, further comprising at least one polyoxyalkylenated silicone elastomer.

16. The composition according to claim 1, further comprising at least one hydrophobic coated pigment.

17. The composition according to claim 16, wherein the at least one hydrophobic coated pigment is at least one selected from the group consisting of a metal oxide, manganese violet, ultramarine blue, Prussian blue, ferric blue, bismuth oxychloride, mother-of-pearl, mica covered with titanium oxide or with bismuth oxychloride, a colored pearlescent pigment and a mixture thereof.

18. The composition according to claim 16, wherein a content of the at least one hydrophobic coated pigment is from 0.5 to 20% by weight with respect to the total weight of the composition.

19. The composition according to claim 1, wherein the fatty phase comprises from 15% to 40% by weight of volatile oil(s), with respect to the total weight of the composition.

20. A cosmetic method for non-therapeutically making up the skin, comprising:

applying to the skin, the cosmetic composition according to claim 1.

21. The composition according to claim 1, wherein the viscosity, measured at 25° C. at a shear rate of 200 $min^{-1}$, is from 0.4 to 0.8 Pa.s.

* * * * *